US00PP24456P3

(12) United States Plant Patent
Villegas

(10) Patent No.: US PP24,456 P3
(45) Date of Patent: May 13, 2014

(54) *SANSEVIERIA* PLANT NAMED 'WHITNEY'

(50) Latin Name: *Sansevieria trifasciata*
Varietal Denomination: Whitney

(75) Inventor: Marvin Gonzalez Villegas, San Ramon (CR)

(73) Assignee: Florica Farms, Inc., Eustis, FL (US)

( * ) Notice: Subject to any disclaimer, the term of this patent is extended or adjusted under 35 U.S.C. 154(b) by 0 days.

(21) Appl. No.: 13/374,903

(22) Filed: Jan. 23, 2012

(65) Prior Publication Data

US 2013/0191953 P1 Jul. 25, 2013

(51) Int. Cl.
*A01H 5/00* (2006.01)

(52) U.S. Cl.
USPC ..... Plt./382

(58) Field of Classification Search
USPC ..... Plt./382, 263.1, 226
See application file for complete search history.

*Primary Examiner* — Kent L Bell
(74) *Attorney, Agent, or Firm* — Foley & Lardner LLP

(57) ABSTRACT

The Whitney variety belongs to the "compact *Sansevieria* group", with a plant height of 37-41 cm, and an average of 4-5 leaves per plant. The plant shape is an inverted pyramid and the arrangement of the leaves is in the form of a rosette. Present dark green color in the center of the blades with wide and variegated margins with irregular pale green and dark green thin bands.

3 Drawing Sheets

Latin name of the genus and species of the claimed plant: *Sansevieria trifasciata.*

Cultivar denomination: 'Whitney'.

BACKGROUND OF THE INVENTION

The present invention relates to a new and distinct cultivar of *Sansevieria* plant, botanically known as *Sansevieria trifasciata*, of the family Ruscaceae, hereinafter referred to by the cultivar name 'Whitney'

*Sansevieria* is a monocotyledonous and succulent, flowering plant which can be produced in either hard-leafed or soft-leafed varieties for interior use as a house plant or outdoor ornamental plant.

The new *Sansevieria* 'Whitney' was discovered and selected by Mr. Marvin Gonzalez Villegas, as a single flowering plant within a planting of 'Black Gold Superba' at Monterrey, San Carlos, Alajuela province, Costa Rica in 2006. It originated as a naturally-occurring mutation of the *Sansevieria* variety 'Black Gold Superba' (unpatented).

Asexual reproduction of the new *Sansevieria* cultivar by vegetative cuttings was first performed in January 2007 in Monterrey, San Carlos, Alajuela, Costa Rica and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'Whitney', which in combination distinguish this *Sansevieria* as a new and distinct cultivar:

1. Dark green-colored foliage with variegated margins (dark green and pale green), no stripes;
2. Wide, long (34 cm) lanceolate leaves, in a basal rosette.
3. 37-41 cm plant height.

4. Erect plant habit.
5. Needs little water and is very drought tolerant.

The new cultivar 'Whitney' is considered a variation of *Sansevieria* in the group denominated as "compact *Sansevieria* plants". The claimed cultivar presents an average of 4-5 leaves per plant when it reaches its maturity (between 7-8 months). The new variety has an erect growth habit and the entire plant can reach 37 to 41 cm height. Its leaves are narrow (8.5 cm average measured at the widest part of the mature leaf) and lanceolate, with a soft waxy texture and the blades are thin and slightly wavy. The plant has an inverted triangle shape.

This variety is very drought tolerant and adapts to conditions of light and shade (interior and exterior).

The leaf blade is dark green (RHS 132A), and has 1.5 cm margins on both sides of the leaf. These margins are variegated with irregular horizontal stripes alternating the main color with pale green (RHS 130D) wider stripes in young leaves. This color becomes light yellowish green (RHS 142D and RHS 139D) in mature leaves. In the fully mature leaves, the base displays a bright yellow-green color (RHS 150A).

Plants of the new *Sansevieria* 'Whitney' differ from plants of the parental cultivar 'Black Gold Superba' (unpatented) in the characteristics described in Table 1.

The new *Sansevieria* 'Whitney' originated as a naturally-ocurring variation (mutation) of the *Sansevieria* 'Black Gold Superba'. The variety 'Black Gold Superba' is also considered to be part of the "compact *Sansevieria* group". It shows less vigor than 'Whitney', has fewer leaves per plant (3-4), with an average leaf width of 6.5 cm (measured in the middle of the mature leaf.) The growth habit is erect and presents wide leaves supported in a rosette. The entire plant can reach a size between 30-40 cm, and the plant has, as for 'Whitney', an inverted triangle shape. The leaves are lanceolate with a soft, waxy texture. The younger leaves show a yellowish-green vivid coloration (RHS 134A) in the interior of the leaf blade. This area also has irregular streaks of yellowish-green bands (RHS 142D), and there are margins on both sides of the leaf which are variegated with irregular horizontal bands that alternate between light yellowish green (RHS 142D) broad bands and brilliant yellowish green (RHS 149A) thin bands. When the leaf is mature the deep color inside turns dark green (RHS 132A), while margins alternate between dark green (RHS 132A) and very pale green (RHS 130A) colors.

TABLE 1

Comparison with Parental Variety

| Characteristic | New Cultivar 'Whitney' | Female Parent 'Black Gold Superba' (unpatented) |
|---|---|---|
| Plant Vigor | more vigorous (more leaves) | less vigorous (less leaves) |
| Color | Dark green leaves with variegated margins (alternating pale green and dark green bands) | green leaves with yellow margins. |
| Shape | wide and lanceolate leaves on a rosette | wide and lanceolate leaves |
| Texture of leaves | smooth-textured leaves | smooth-textured leaves |

Of the many commercial cultivars known to the present inventor, the most similar in comparison to the new *Sansevieria* 'Whitney' is the *Sansevieria trifasciata* var. 'Black Robusta' (unpatented), in the characteristics described in Table 2

'Black Robusta' is described as a variety with a medium vigor, has a growth rate between 16-40 cm, and a quantity of 3-5 leaves per plant. The leaves are wide (8 cm in the widest part of the mature leaf) and lanceolate. The leaf maintains the same coloration in both upper and under sides. It has a uniform dark green color (RHS 139A) with stripes distributed throughout, with brilliant yellowish-green color (RHS 142B). The plant has an inverted triangle shape. As with other varieties of *Sansevieria*, this variety shows a high adaptability to conditions of light and shade, as well as tolerance to different water stress conditions.

TABLE 2

Comparison with Comparison Cultivar

| Characteristic | New Cultivar 'Whitney' | Comparison Cultivar 'BLACK ROBUSTA' (unpatented) |
|---|---|---|
| Plant Vigor | more vigor (4-5 leaves per plant) | less vigor (3-4 leaves per plant) similar size |
| Color | dark green foliage with variegated margins (dark green and pale green) | dark green foliage, with pale green irregulars stripes. |
| Shape | wide and lanceolate leaves on a rosette | wide and lanceolate leaves on a rosette |
| Texture of leaves leaves | smooth and waxy textured leaves | smooth and waxy textured leaves |

BRIEF DESCRIPTION OF THE PHOTOGRAPHS

The accompanying photographs illustrate the overall appearance of the new *Sansevieria* cultivar 'Whitney' showing the colors as true as is reasonably possible with colored reproductions of this type. Colors in the photographs may differ slightly from the color value cited in the detailed botanical description which accurately describe the color of 'Whitney'.

DETAILED BOTANICAL DESCRIPTION

Figure 1:
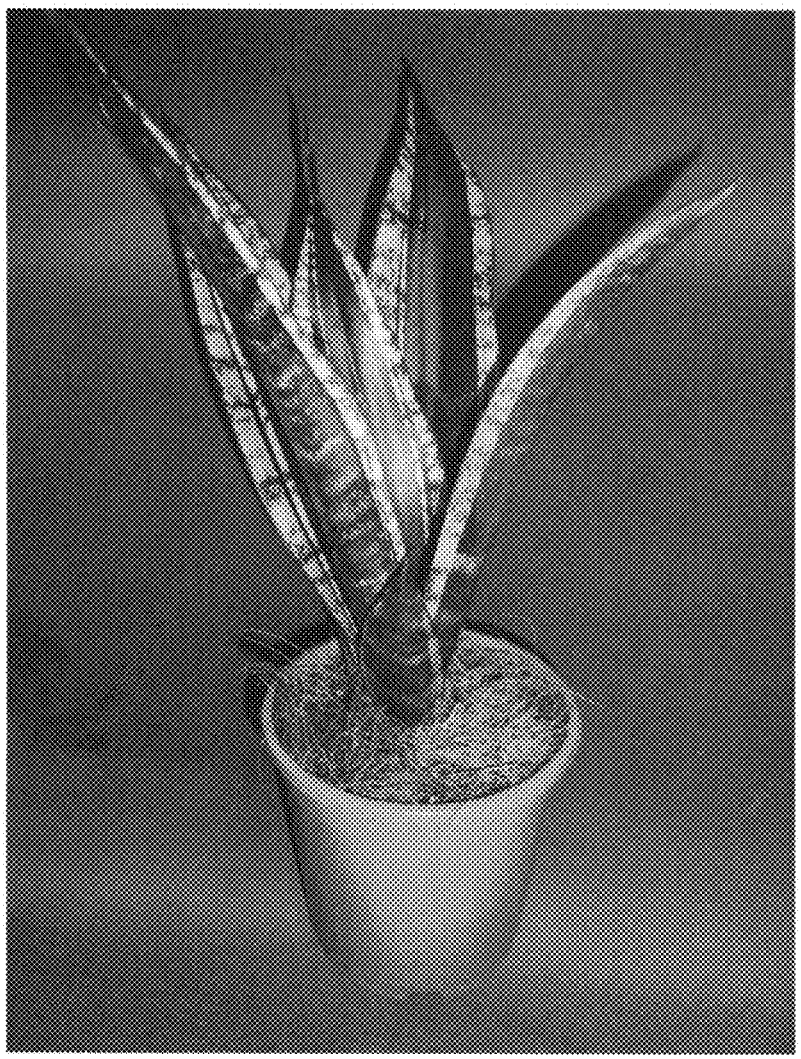
FIG. 1 Shows a side view of an eight month old plant of *Sansevieria* 'Whitney' in a 21 cm diameter pot.
Figure 2:
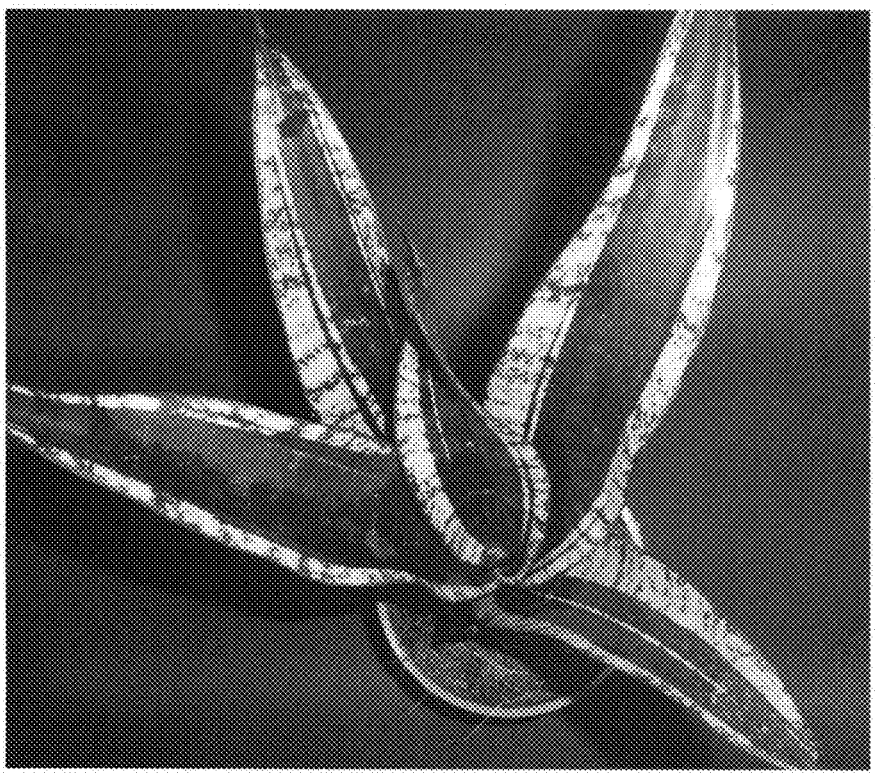
FIG. 2 shows a top view of an eight month old plant of *Sansevieria* 'Whitney' in a 21 cm diameter pot.
Figure 3A:
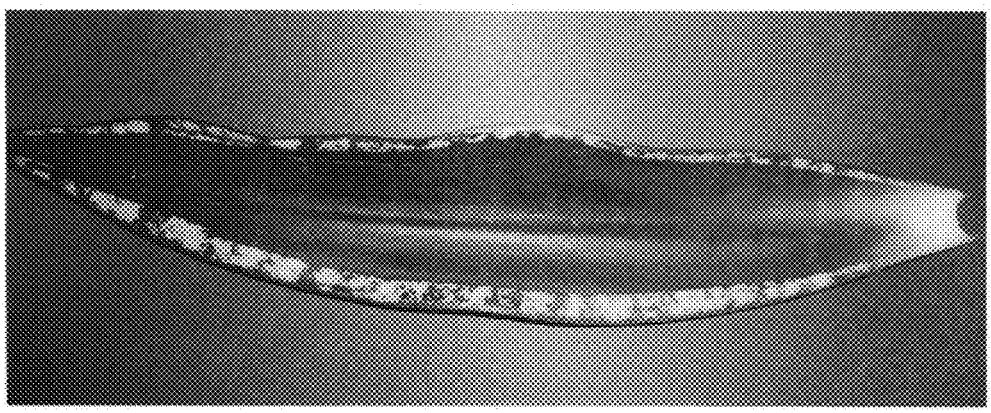
FIG. 3A Shows a close-up view of the upper side of a typical leaf of 'Whitney', taken from an eight-month old plant.
Figure 3B:
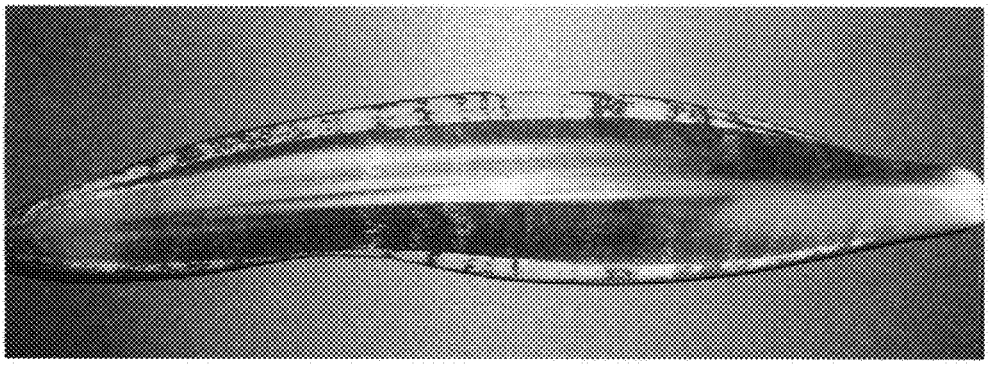
FIG. 3B Shows a close-up view of the lower side of a typical leaf of 'Whitney', taken from an eight-month old plant.

The new *Sansevieria* 'Whitney' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Sansevieria* cultivar 'Whitney' as grown in an open-field at Monterrey, San Carlos de Alajuela province, Costa Rica, conditions which closely approximate those generally used in commercial practice. Average temperature in Monterrey is 24.5° C. during the day and 18° C. at night. Plants grow under natural light conditions.

This crop does not require constant fertilization, however to increase production per area about 200 kg $ha^{-1}$ N, 150 kg $ha^{-1}$ of P and 100 kg $ha^{-1}$ K are required. Production is closely related with soil conditions in which the plants are grown.

Color references are made to The Royal Horticultural Society Color Chart (R.H.S.), (April 2009) except where general colors of ordinary significance are used.

The photographs and descriptions were taken during the rainy season in Monterrey, San Carlos, Alajuela province, Costa Rica when outdoor day temperature was 23° C. The age of the plants described is 8 months.

Classification:

*Botanical.*—*Sansevieria trifasciata.*

*Variety denomination.*—Whitney.

Parentage: *Sansevieria trifasciata*, 'Black Gold Superba' (unpatented).

Optimal growth conditions:

*Light intensities.*—High adaptability to outdoor or indoor conditions.

*Temperature.*—Day: 24° C. to 32° C. Night: 18° C. to 23° C.

*Temperature tolerance.*—Tolerant to a low temperature of about 12° C. and tolerant to a high temperature of about 35° C.

*Fertilization.*—200, 150 and 100 kg $ha^{-1}$ of N, P and K.

*Growth regulators.*—Not necessary.

Propagation:

*Type.*—Vegetative, by rooted cuttings.

*Rooting habit and description.*—Rhizomes, with short roots.

*Time to initiate roots.*—15 to 22 days at 18-25° C.

*Time to produce a rooted cutting.*—About 60 to 90 days at 18-25° C.

Plant:

*General appearance and form.*—Height: About 41 cm when grown in ground; About 37 cm when grown in a 21 cm size container. Spread: About 11 cm when grown in ground; About 10 cm when grown in 21 cm size container. Form: Monocot; leaf bases arranged in a rosette around growth point. Shape: inverted triangle.

*Growth rate and habit.*—About 2 cm per week; upright.

*Fragrance.*—None.

*Stem.*—Modified (Rhizome and Foliage). Length: About 12 cm when grown in ground; About 5 cm when grown in 21 cm size container. Diameter: About 2 cm to 3.5 cm. Shape: round. Texture: Rough. Color: RHS 17A. Strength: strong and durable. Internode length: About 1 mm to 3 mm.

Foliage:

*Quantity.*—About 4-5.

*Arrangement and attachment.*—Single, alternate; leaf bases arranged in a rosette around growth point.

*Leaf length.*—About 34 cm.

*Leaf width.*—About 8.5 cm.

*Overall shape of leaf.*—Lanceolate.

*Apex shape.*—Acute, triangular.

*Base shape.*—Plane.

*Margin.*—Sharp, smooth.

*Texture.*—Upper Surface: smooth and waxy texture. Under Surface: smooth and waxy texture.

*Pubescence.*—None.

*Color of mature leaf.*—Upper Surface: RHS132A, Margins: irregular bands of RHS132A and RHS139D. Lower Surface: RHS134A, Margins: irregular bands of RHS142D and RHS139A.

*Color of immature leaf.*—Upper Surface: RHS139A on the leaf surface, Margins: variegated with bands of RHS 130D and RHS139A. Lower Surface: RHS 139A on the leaf surface, Margins: variegated with bands of RHS 130D and RHS139A.

*Venation.*—Pattern: longitudinal/parallel leaf shape.

*Leaf fragrance.*—None.

Inflorescence description:

*Arrangement and type.*—Inflorescence.

*Orientation at opening.*—Out of the spike.

*Quantity.*—About 22 opened flowers per spike 2 weeks after appearance of the spike. Flowers sporadically but profusely under growth conditions.

*Per plant with at least one open flower.*—One inflorescence per plant.

*Inflorescence size.*—Length: About 28 cm. Diameter: About 4 cm.

*Flower size.*—Length: About 2 cm. Diameter: About 1.0 cm. Depth: About 1 cm.

*Fragrance.*—Soft and pleasant.

*Bud.*—Rate of opening: About 7 to 8 days, according to weather. Shape: ovoid. Length: About 2 cm. Diameter: About 3.0 mm. Color: Apex: RHS 150A. Base: RHS 142A. Texture (both surfaces): smooth.

Petals:

*Quantity.*—6. No further data on the instant plant's petals was collected.

*Arrangement.*—Star-shaped.

Reproductive organs:

*Androecium.*—Stamen: Number: 5 per flower. Length: About 1.3 cm. Color: RHS 150C. Anther: Length: About 0.2 mm. Width: About 0.1 mm. Color: RHS 150C. Filament: Length: About 1.1 mm. Color: RHS 150C. Pollen: Amount: moderate. Color: RHS 154D.

*Gynoecium.*—Pistil: Number: One per flower. Length: About 2.1 cm. Stigma: Length: About 0.6 mm. Width: About 0.8 mm. Color: RHS 150C. Style: Length: About 1.3 mm. Color: RHS 150C. Ovary: Length: About 3 mm. Width: About 2.5 mm. Color: RHS 150C.

*Fruits.*—Not observed so far.

Weather resistance: Drought tolerant.

Disease/pest resistance: Not observed for disease/pest resistance.

Disease/pest susceptibility: Not observed for disease/pest susceptibility.

I claim:

1. A new and distinct variety of *Sansevieria* plant named 'WHITNEY', substantially as illustrated and described herein.

* * * * *